(12) United States Patent
Casimiro et al.

(10) Patent No.: US 6,572,857 B1
(45) Date of Patent: Jun. 3, 2003

(54) ANTI-CD6 MONOCLONAL ANTIBODIES AND THEIR USES

(75) Inventors: Jose Enrique Montero Casimiro, Habana (CU); Josefa Lombardero Valladares, Habana (CU); Rolando Perez Rodriguez, Habana (CU); Patricia Sierra Blazquez, Habana (CU); Rosa Blanca Tormo Bravo, Habana (CU)

(73) Assignee: Centro de Inmunologia Molecular (CIM)

( * ) Notice: Subject to any disclaimer, the term of this patent is extended or adjusted under 35 U.S.C. 154(b) by 0 days.

(21) Appl. No.: 08/875,674

(22) PCT Filed: Nov. 18, 1996

(86) PCT No.: PCT/CU96/00004

§ 371 (c)(1),
(2), (4) Date: Dec. 17, 1997

(87) PCT Pub. No.: WO97/19111

PCT Pub. Date: May 29, 1997

(30) Foreign Application Priority Data

Nov. 8, 1996 (WO) .............................. PCT/CU96/00004
Nov. 17, 1997 (CU) ................................................ 120/95

(51) Int. Cl.[7] ............................................ A61K 39/395
(52) U.S. Cl. ................................ 424/133.1; 424/143.1; 530/388.22; 436/548
(58) Field of Search .......................... 530/387.5, 387.7, 530/388.1, 387.1, 387.2, 388.15, 388.22; 436/548, 133.1; 424/143.1

(56) References Cited

U.S. PATENT DOCUMENTS 5,723,437 A * 3/1998 Haynes et al. .................. 514/2

OTHER PUBLICATIONS

Limonta et al., Immunotechnology 1 (1995) 107–113.*
Osorio et al., Cellular Immunology 154, 123–133,1994.*

* cited by examiner

Primary Examiner—Laurie Scheiner
(74) Attorney, Agent, or Firm—Lackenbach Siegel LLP

(57) ABSTRACT

Monoclonal antibodies that recognize the CD6 antigen, pharmaceutical compositions that recognizes and that are able to achieve a clinical and histological effectivity in patients with different clinical types of Psoriasis.

7 Claims, 8 Drawing Sheets

FIG. 1A

|   | 1 | 2 | 3 | 4 | 5 | 6 | 7 | 8 | 9 | 10 | 11 | 12 |
|---|---|---|---|---|---|---|---|---|---|----|----|----|
| A | GLU | VAL | GLN | LEU | VAL | GLU | SER | GLY | GLY | GLY | LEU | VAL |
| B | GLU | VAL | GLN | LEU | VAL | GLU | SER | GLY | GLY | GLY | LEU | VAL |
| C | GLU | VAL | GLN | LEU | VAL | GLU | SER | GLY | GLY | GLY | LEU | VAL |

|   | 13 | 14 | 15 | 16 | 17 | 18 | 19 | 20 | 21 | 22 | 23 | 24 |
|---|----|----|----|----|----|----|----|----|----|----|----|----|
| A | LYS | PRO | GLY | GLY | SER | LEU | LYS | LEU | SER | CYS | ALA | ALA |
| B | GLN | PRO | GLY | GLY | SER | LEU | ARG | LEU | SER | CYS | ALA | ALA |
| C | LYS | PRO | GLY | GLY | SER | LEU | LYS | LEU | SER | CYS | ALA | ALA |

|   | 25 | 26 | 27 | 28 | 29 | 30 | 31 | 32 | 33 | 34 | 35 | 36 |
|---|----|----|----|----|----|----|----|----|----|----|----|----|
| A | SER | GLY | PHE | LYS | PHE | SER | ARG | TYR | ALA | MET | SER | TRP |
| B | SER | GLY | PHE | THR | PHE | SER | ARG | TYR | ALA | MET | SER | TRP |
| C | SER | GLY | PHE | LYS | PHE | SER | ARG | TYR | ALA | MET | SER | TRP |

|   | 37 | 38 | 39 | 40 | 41 | 42 | 43 | 44 | 45 | 46 | 47 | 48 |
|---|----|----|----|----|----|----|----|----|----|----|----|----|
| A | VAL | ARG | GLN | THR | PRO | GLU | LYS | ARG | LEU | GLU | TRP | VAL |
| B | VAL | ARG | GLN | ALA | PRO | GLY | LYS | GLY | LEU | GLU | TRP | VAL |
| C | VAL | ARG | GLN | ALA | PRO | GLY | LYS | ARG | LEU | GLU | TRP | VAL |

|   | 49 | 50 | 51 | 52 | 53 | 54 | 55 | 56 | 57 | 58 | 59 |
|---|----|----|----|----|----|----|----|----|----|----|----|
| A | ALA | THR | ILE | SER | SER | GLY | GLY | SER | TYR | ILE | TYR |
| B | SER |     |     |     |     | GLY | GLY | SER | TYR | ILE | TYR |
| C | ALA | THR | ILE | SER | SER | GLY | GLY | SER | TYR | ILE | TYR |

```
            60                                              71
      A    PRO  ASP  SER  VAL  LYS  GLY  ARG  PHE  THR  ILE  SER  ARG
      B    PRO  ASP  SER  VAL  LYS  GLY  ARG  PHE  THR  ILE  SER  ARG
      C    PRO  ASP  SER  VAL  LYS  GLY  ARG  PHE  THR  ILE  SER  ARG
            72                                                    82A

A    ASP  ASN  VAL  LYS  ASN  THR  LEU  TYR  LEU  GLN  MET  SER
      B    ASP  ASN  SER  LYS  ASN  THR  LEU  TYR  LEU  GLN  MET  ASN
      C    ASP  ASN  VAL  LYS  ASN  THR  LEU  TYR  LEU  GLN  MET  SER
            82B                                                    92

A    SER  LEU  ARG  SER  GLU  ASP  THR  ALA  MET  TYR  TYR  CYS
      B    SER  LEU  ARG  ALA  GLU  ASP  THR  ALA  VAL  TYR  TYR  CYS
      C    SER  LEU  ARG  SER  GLU  ASP  THR  ALA  MET  TYR  TYR  CYS
            93                                                    102

A    ALA  ARG  ARG  ASP  TYR  ASP  LEU  ASP  TYR  PHE  ASP  SER
      B    ALA  LYS  ARG  ASP  TYR  ASP  LEU  ASP  TYR  PHE  ASP  SER
      C    ALA  ARG  ARG  ASP  TYR  ASP  LEU  LEU  TYR  PHE  ASP  SER
            103                 108  109                          113

A    TRP  GLY  GLN  GLY  THR  VAL  VAL  SER  SER
      B    TRP  GLY  GLN  GLY  THR  LEU  VAL  SER  SER
      C    TRP  GLY  GLN  GLY  THR  LEU  VAL  SER  SER
```

FIG.2

| FIG.2A |
|--------|
| FIG.2B |

FIG.2A

|   |   |   |   |   |   |   |   |   |   |   | 11 | 12 |
|---|---|---|---|---|---|---|---|---|---|---|----|----|
| A | ASP | ILE | LYS | MET | THR | GLN | SER | PRO | SER | SER | MET | TYR |
| B | ASP | ILE | GLN | MET | THR | GLN | SER | PRO | SER | SER | LEU | SER |
| C | ASP | ILE | |GLN| | MET | THR | GLN | SER | PRO | SER | SER | |LEU| | SER |
|   | 13 |   | 15 |   | 17 |   |   |   |   |   |    | 24 |
| A | ALA | SER | LEU | GLY | GLU | ARG | VAL | THR | ILE | THR | CYS | LYS |
| B | ALA | SER | VAL | GLY | ASP | ARG | VAL | THR | ILE | THR | CYS | |
| C | ALA | SER | |VAL| | GLY | |ASP| | ARG | VAL | THR | ILE | THR | CYS | LYS |
|   | 25 |   |   |   |   |   |   |   |   |   |    | 36 |
| A | ALA | SER | ARG | ASP | ILE | ARG | SER | TYR | LEU | THR | TRP | TYR |
| B |   |   |   |   |   |   |   |   |   |   | TRP | TYR |
| C | ALA | SER | ARG | ASP | ILE | ARG | SER | TYR | LEU | THR | TRP | TYR |
|   | 37 |   |   |   | 41 |   | 43 |   |   |   |    | 48 |
| A | GLN | GLN | LYS | PRO | TRP | LYS | SER | PRO | LYS | THR | LEU | ILE |
| B | GLN | GLN | LYS | PRO | GLY | LYS | ALA | PRO | LYS | LEU | LEU | ILE |
| C | GLN | GLN | LYS | PRO | |GLY| | LYS | |ALA| | PRO | LYS | THR | LEU | ILE |
|   | 49 |   |   |   |   |   |   |   |   |   |    | 60 |
| A | TYR | TYR | ALA | THR | SER | LEU | ALA | ASP | GLY | VAL | PRO | SER |
| B | TYR |   |   |   |   |   |   |   | GLY | VAL | PRO | SER |
| C | TYR | TYR | ALA | THR | SER | LEU | ALA | ASP | GLY | VAL | PRO | SER |

|     |     |     |     |     |     |     |     |     |     |     |     |
|-----|-----|-----|-----|-----|-----|-----|-----|-----|-----|-----|-----|
| 61  |     |     |     |     |     |     |     |     |     |     | 72  |
| A   | ARG | PHE | SER | GLY | SER | GLY | GLN | ASP | TYR | SER |
| B   | ARG | PHE | SER | GLY | SER | GLY | THR | ASP | PHE | THR |
| C   | ARG | PHE | SER | GLY | SER | GLY | GLN | ASP | TYR | SER |
| 73  |     |     |     |     |     |     |     |     |     |     | 84  |
| A   | LEU | THR | ILE | SER | SER | LEU | GLU | ASP | THR | ALA |
| B   | LEU | THR | ILE | SER | SER | LEU | GLN | ASP | PHE | ALA |
| C   | LEU | THR | ILE | SER | SER | LEU | GLU | ASP | THR | ALA |
| 85  |     |     |     |     |     |     |     |     |     |     | 96  |
| A   | THR | TYR | TYR | CYS | LEU | GLN | HIS | GLY | SER | PRO | PHE |
| B   | THR | TYR | TYR | CYS |     |     |     |     |     |     |     |
| C   | THR | TYR | TYR | CYS | LEU | GLN | HIS | GLY | GLU | SER | PRO | PHE |
| 97  |     |     |     |     |     |     |     |     |     |     | 108 |
| A   | THR | PHE | GLY | SER | GLY | THR | LYS | LEU | GLU | ILE | LYS | ARG |
| B   | THR | PHE | GLY | GLN | GLY | THR | LYS | LEU | GLU | ILE | LYS | ARG |
| C   | THR | PHE | GLY | SER | GLY | THR | LYS | LEU | GLU | ILE | LYS | ARG |
| 109 |     |     |
| A   | ALA |
| B   | THR |
| C   | ALA |

FIG.2B

| PATIENT | CD6 EXPRESSION | HISTOLOGICAL DIAGNOSIS |
|---|---|---|
| 1. IRM | +++ | PSORIASIS VULGAR |
| 2. ZEAP | +++ | PSORIASIS VULGAR |
| 3. DLH | +++ | PSORIASIS VULGAR |
| 4. JMV | +++ | PSORIASIS VULGAR |
| 5. MCGH | +++ | PSORIASIS VULGAR |
| 6. DMMG | +++ | PSORIASIS VULGAR |
| 7. ACP | +++ | PSORIASIS VULGAR |
| 8. CCD | +++ | PSORIASIS VULGAR |
| 9. MPC | +++ | PSORIASIS VULGAR |
| 10. NRG | +++ | PSORIASIS VULGAR |
| 11. MVMH | +++ | PSORIASIS VULGAR |
| 12. IMVR | +++ | PSORIASIS VULGAR |
| 13. MEGA | +++ | PSORIASIS VULGAR |
| 14. CBT | +++ | PSORIASIS VULGAR |

FIG.3

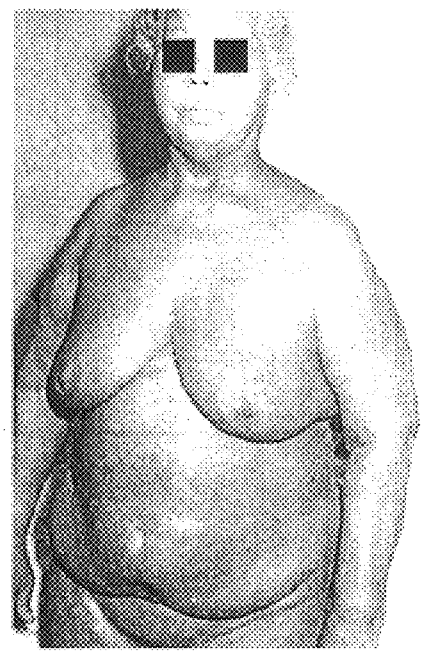
FIG.6

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 119 Amino acid residues.
      (B) TYPE: Amino acid.
      (C) STRANDEDNESS: Unknown.
      (D) TOPOLOGY: Unknown.

(ii) MOLECULE TYPE: Protein (iii) HYPOTHETICAL: No (iv) ANTI-SENSE: No (v) FRAGMENT TYPE: -N Terminal fragment.

(vi) ORIGINAL SOURCE:
      (A) ORGANISM: Mice Balb/C
      (C) INDIVIDUAL ISOLATE: ior t1A
      (F) TISSUE TYPE: Murine hibridoma (vii) IMMEDIATE SOURCE:
      (B) CLONE: Sub-clone ior t1A (ix) FEATURE:
    (C) IDENTIFICATION METHOD: Experimental.
    (D) OTHER INFORMATION: Sequence corresponding to the variable region of the heavy chain of the monoclonal antibody recognizing human CD6, designated as sub-clone ior t1A.

(xi) SEQUENCE DESCRIPTION: SEQ ID NO: 1:

```
Glu Val Gln Leu Val Glu Ser Gly Gly Leu Val Lys Pro Gly Gly
1               5                  10                  15

Ser Leu Lys Leu Ser Cys Ala Ala Ser Gly Phe Lys Phe Ser Arg Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Thr Leu Thr Val Ser Ser
            115
```

(2) INFORMATION FOR SEQ ID NO: 2:

(i) SEQUENCE CHARACTERISTICS:
        (A) LENGTH: 109 Amino acid residues.
        (B) TYPE: Amino acid.
        (C) STRANDEDNESS: Unknown.
        (D) TOPOLOGY: Unknown.

(ii) MOLECULE TYPE: Protein (iii) HYPOTHETICAL: Yes (iv) ANTI-SENSE: No (v) FRAGMENT TYPE: -N Terminal fragment.

(vi) ORIGINAL SOURCE:
        (A) ORGANISM: Mice Balb/C
        (C) INDIVIDUAL ISOLATE: ior t1A
        (F) TISSUE TYPE: Murine hibridoma (vii) IMMEDIATE SOURCE:
        (B) CLONE: Sub-clone ior t1A (ix) FEATURE:
        (C) IDENTIFICATION METHOD: Experimental.
        (D) OTHER INFORMATION: Sequence corresponding to the variable region of the light chain of the monoclonal antibody recognizing human CD6, designated as sub-clone ior t1A.

(xi) SEQUENCE DESCRIPTION: SEQ ID NO: 2:

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Arg Asp Ile Arg Ser Tyr
                20                  25                  30

Leu Thr Trp Tyr Gln Gln Lys Pro Trp Lys Ser Pro Lys Thr Leu Ile
            35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80
```

Asp Asp Thr Ala Thr Tyr Tyr Cys Leu Gln His Gly Glu Ser Pro Phe
            85                  90                  95

Thr Phe Gly Ser Gly Thr Lys Leu Glu Ile Lys Arg Ala
            100                 105

(2) INFORMATION FOR SEQ ID NO:3:

(i) SEQUENCE CHARACTERISTICS:
        (A) LENGTH: 119 Amino acid residues.
        (B) TYPE: Amino acid.
        (C) STRANDEDNESS: Unknown.
        (D) TOPOLOGY: Unknown.

(ii) MOLECULE TYPE: Protein (iii) HYPOTHETICAL: No (iv) ANTI-SENSE: No (v) FRAGMENT TYPE: -N Terminal fragment.

(vi) ORIGINAL SOURCE:
        (F) TISSUE TYPE: Animal cells.
        (G) CELL LINE: NSO " SP 2/0 " CHO (vii) IMMEDIATE SOURCE:
        (B) CLONE: Sub-clone ior t1A (ix) FEATURE:
        (C) IDENTIFICATION METHOD: By similarity with known sequence.
        (D) OTHER INFORMATION: Sequence corresponding to the
            humanized variant of sub-clone ior t1A recognizing human
            CD6, particularly to the variable region of its heavy
            chain.

(xi) SEQUENCE DESCRIPTION: SEQ ID NO: 3:

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
            35                  40                  45

Ala Thr Ile Ser Ser Gly Gly Ser Tyr Ile Tyr Tyr Pro Asp Ser Val
            50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
            85                  90                  95

Ala Arg Arg Asp Tyr Asp Leu Asp Tyr Phe Asp Ser Trp Gly Gln Gly
            100                 105                 110

Thr Leu Val Thr Val Ser Ser
            115

(2) INFORMATION FOR SEQ ID NO:4:

(i) SEQUENCE CHARACTERISTICS:
        (A) LENGTH: 109 Amino acid residues.
        (B) TYPE: Amino acid.
        (C) STRANDEDNESS: Unknown.
        (D) TOPOLOGY: Unknown.

(ii) MOLECULE TYPE: Protein (iii) HYPOTHETICAL: No (iv) ANTI-SENSE: No

-continued

```
    (v) FRAGMENT TYPE: -N Terminal fragment.

(vi) ORIGINAL SOURCE:
        (F) TISSUE TYPE:  Animal cells.
        (G) CELL LINE: NSO " SP 2/0 " CHO (vii) IMMEDIATE SOURCE:
        (B) CLONE: Sub-clone ior t1A (ix) FEATURE:
        (C) IDENTIFICATION METHOD: By similarity with known sequence.
        (D) OTHER INFORMATION:  Sequence corresponding to the
            humanized variant of sub-clone ior t1A recognizing human
            CD6, particularly to the variable region of its light
            chain.

(xi) SEQUENCE DESCRIPTION: SEQ ID NO: 4:

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
                20                  25                  30

Leu Thr Trp Tyr Gln Gln Lys Pro Gly Lys Ala Pro Lys Thr Leu Ile
            35                  40                  45

Tyr Tyr  Ala Thr Ser Leu Ala Asp Gly Val Pro Ser Arg Phe Ser Gly
    50                   55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala
                100                 105
```

ANTI-CD6 MONOCLONAL ANTIBODIES AND THEIR USES

FIELD OF THE INVENTION

The present invention is related to the field of immunology and particularly with obtaining a pharmaceutical composition that contains a monoclonal antibody that recognizes the CD6 leukocyte differentiation antigen.

DESCRIPTION OF THE PRIOR ART

Monoclonal antibodies (mAbs) have permitted the characterization of molecules of physiological importance expressed on the cell surface. Defined in the cells of the Immune System the "Leukocyte Differentiation Clusters" or antigens (CD) (scholossman, S. F. et al. (1994) Immunol. Today 15 (3);98). The definition of the role of the CD's in the differentiation and maturation of the lymphoid cells during their ontogenic development, in the mechanisms of cellular recognition and adhesion and in the mechanisms of activation and proliferation during the immune response have conducted to the use of their respective mAbs in diagnosis and immunotherapy, with promising results (Dantal, J. et al. (1991) Curr. Opin. Immunol. 3:740).

The murine mAbs directed against molecules expressed on the cell membrane of human T lymphocytes have contributed to improve the diagnosis of clinical entities in which there is dysfunction of these cells. Moreover they have been used to explore new therapeutic approachs with the purpose of modulating their functional activity as in the cases of Transplant Rejection, Graft Versus Host Disease (GvHD) and Autoimmune Diseases (Waldman, T. A. (1991) Science 252:1657; Waldman, T. A. (1992) Annu. Rev. Immunol. 10: 675).

The CD6 is a not well characterized molecule. It is known that it is a glycoprotein existing in two molecular forms maintained in dynamic equilibrium and differing only in the grade of phosphorylation. In the resting T lymphocytes it is a phosphorylated molecule of 105 kDa, while in activated cells it is a hyperphosphorylated form of 130 kDa (Cardenas, L. et al. (1990) J. Immunol. 145:1450; Swack, J. A. et al. (1991) J. Biol. Chem. 266: 7137), member of a family of membrane receptors and secretion proteins with a characteristic structure (Kodama, T. et al. (1990) Nature 343: 531; Aruffo, A. et al. (1991) J. Exp. Med. 174: 949). It is expressed on the surface of mature human thymocytes, in T lymphocytes of peripheral blood, constituting the majority of the CD3+ cell population, in a subtype of B lymphocytes and in the neurons of the brain cortex. In the T lymphocytes of peripheral blood it participates in the mechanisms of cellular activation (Reinhertz, E. L. et al. (1982) Cell 30: 735; Kamoun, M. et al (1981) J. Immunol. 127: 987; Mayer, B. et al. (1990) J. Neuroimmunol. 29: 193; Rasmussen, R. A. et al. (1994) J. Immunol. 152: 527).

The role of the CD6 molecule in the T cell ontogenesis as well as its possible role in the physiopathology of diseases of different etiology are unknown.

Recently a CD6 ligand was identified and characterized having an extensive cellular distribution in normal tissues such as thymus, spleen, lymph nodes, and skin (Dhavalkumar, D. P. et al. (1995) J. Exp. Med. 181:1563). This molecule, denominated ALCAM (Activated Leukocyte-Cell Adhesion Molecule due to its expression in activated T and B lymphocytes as well as monocytes, is a 100 kDa molecular weight type I membrane glycoprotein with five extracellular domains similar to those of the immunoglobulins. It can present different activation levels depending on divalent cations and can mediated heterophylic and homophylic interactions (Bowen, M. A. et al. (1995) J. Exp Med. 181: 2213).

Different anti CD6 mAbs have been used in clinical research for the prevention of the rejection crisis in organ transplantation (Kirkman, R. L. et al. (1983) Transplantation 36: 620) and to deplete bone marrow transplants from lymphocytes for preventing Graft versus Host Disease (GVHD) (Soiffer, R. J. et al. (1992) J. Clin. Oncol. 10:1191). The ior t1 mAb is in a Phase II Clinical Trial for the treatment of Cutaneous T-Cell Lymphomas (Garcia, C. A. et al. (1990) Biotecnologia Aplicada 7(2):176; Faxas, M. E. et al (1993) Biotecnologia Aplicada 10(1): 20).

The ior t1 monoclonal antibody of IgG2a isotype was classified as anti CD6 in the IV international Workshop of Leucocyte Differentiation Antigens, Vienna (1989). This mAb defines an epitope different from the ones recognized by other anti CD6 mAbs. The epitope has a stable conformation and is insensitive to reduction agents, being possibly located in the primary structure of the CD6 molecule (Osorio, L. M. et al. (1994) Cell Immunol. 154:123).

This monoclonal antibody has a lower recognition than other CD6 mAbs in peripheral mononuclear cells of healthy donors. The recognition pattern of ior t1 mAb in human cell culture lines of T lymphocytes origin is 47% in Jurkat cells, 23% in Molt-4 cells and no recognition of CCRF-CEM cells; of B lymphocytes origin is 9% in Raji, of erythroblastoid origin is 12% in K-562 and of myelomonocytic origin is 9% in U-937. It also recognizes peripheral mononuclear cells of Chronic B Lymphocytic Leukemia (89+/−4%) (Garcia C. A. et al. 1992) Biotecnologia Aplicada 9(1):70) and lymphocytes of cutaneous lesions in patients with Cutaneous T-Cell Lymphomas (Rodriguez, T. et al. (1985) Interferon y Biotec. 2(1): 41).

The ior t1 mAb does not inhibit the in vitro antigen specific cellular cytotoxicity (Faxas, M. E. et al. (1993) Biotecnologia Aplicada 10(1):47). It is capable of activating in vitro peripheral blood T lymphocytes of healthy donors. At suboptimum concentrations of OKT3 (anti CD3) the cross-linking with ior t1 induces higher responses than those achieved with other anti CD6 mAbs (Osorio, L. M. et al. (1994) Cell Immunol. 154:123).

Psoriasis is a disease whose physiopathology has not been defined (Hunziker, T. et al. (1993) Ther. Umsch. 50(2);110; Elder, J. T. et al. (1994) J. Invest. Dermatol. 102(6): 24S). It is characterized by presenting an inflammatory infiltrate in the target organ with predominance of activated T lymphocytes of CD4+ and CD8+ phenotypes (Chang, J. C. C. et al. (1994) Proc. Natl. Acad. Sci. USA 91:9282), as well as strong olygoclonality of the T-Cell receptors, the cells seem to present a marked tendency to migrate to the skin (homing) (Baker, J. N. W. N. et al (1992) Br. J. Dermatol. 127; 205; Menssen, A. et al. (1995) J. Immunol. 155:4078; Valdimarsson, H. et al. (1995) Immunol. Today 16(3):145).

The spontaneous remission of Psoriasis can be predicted if the number of T cells in the skin decrease. Thus, it is suggested they play an important role in the perpetuation of the disease by releasing soluble mediators of the immune response capable of inducing the proliferation of keratinocytes, responsible of clinical manifestations of the disease.

These considerations are supported by facts such as the cure of the disease following allogeneic bone marrow transplantation, the possible HLA association, the improvement, with steroids and specially with immunosupressocs like cyclosporine and the clinical improvement, although reversible, with anti T cells therapeutic monoclonal antibodies (Griffiths, C. E. M. et al. (1992) Springer Semin Immunopathol. 13:441; Nanney, L. B. et al. (1986) J. Invest. Dermatol. 86(3): 260; Ficassia, D. D. et al. (1987) J. Am. Acad. Dermatol 17)3: 408; Schopf, R. E. et al. (1986) Arch. Dermatol. Res. 279(2 ): 89; van de Kerkhof, P. C. et al. (1997) Dermatologica 174(5): 224).

The success o immunotherapy with monoclonal antibodies depends on the selection of the target molecule, which should participate in important cellular functions or in the selection of the mAb (Dantal, J. et al. (1991) urr. Opin. Immunol. 3:740). The mAbs evaluated in Psoriasis directed against CD3 (Weinshenker, B. G. at al. (1989) J. Am. Acad. Dermatol. 20:1132) and against CD4 (Poizot-Martin, I. et al. (1991) Lancet 337:1477; Prinz J. et al. (1991) Lancet 338: 320; Nicolas, J. F. et al. (1991) Lancet 338: 321) have produced clinical improvement in the patients after multiple high dose endovenous applications, with partial remissions of short duration and early relapse of the symptoms and signs of the disease in all cases.

Therapeutical application of murine mAbs in multiple doses is associate with some secundary effects and limited clinical utility in patients, these are related with xenogenicity of murine proteins that induce an Human Anti-Mouse Antibodies response (HAMA): humanized antibodies generated by protein engineering have reduced immunogenicity, improved pharmacokinetics and clinical advantage (Winter, G. et al. (1993) Trends-Pharmacol-Sci. 14(5): 139).

Up to now no previous study describing the expression of the CD6 molecule in the T lymphocytes of the inflammatory infiltrate of the skin in Psoriasis nor the possible association of this molecule with the development of the disease has been reported. Additionally the therapeutic use of an anti CD6 n in this disease has not been previously evaluated.

The novelty of the present invention consists in providing topical and systemic pharmaceutical compositions containing an anti CD6 monoclonal antibody and the obtention of an humanized monoclonal antibody anti CD6 for its application in patients with Psoriasis Vulgar, using different administration routes and in different clinical forms of the disease.

DETAILED DESCRIPTION OF THE INVENTION

OBTAINMENT OF THE MONOCLONAL ANTIBODY

Purification of the Murine Monoclonal Antibody.

The anti CD6 monoclonal antibody (mAb) can be purified from ascitis fluid by Protein A Sepharose, diluted with an equal volume of glycine buffer 1.5 M, NaCl 3 M pH 0.9, equilibrating the matrix with the same buffer. Applying equal volumes of ascitis and buffer elution should be performed at flow speed of 50 mL/h. Wash the column overnight until the zero base line, with the same application buffer.

Afterwards the column is washed with citric acid buffer 0.1 M pH 6 to eliminate the IgG1 immunoglobulins, until the base line reaches zero, at a flow speed of 50 mL/h (between 2 and 5 column volumes, approximately 2 hours). Buffer citric acid 0.1 M, pH5 is applied to elute the IgG2a immunoglobulins (ior t1).

Humanization of the Murine Monoclonal Antibody

Using genetic engineering methods variants of the anti CD6 murine mAbs can be constructed, such as chimaeric and humanized antibodies, from the variable regions of the light and heavy chains of the murine antibody (Takashi, N. et al. (1982) Cell 29:718; Hieter, P. A. et al. (1980) Cell 29:718).

Description of Method of Humanization of the Murine Monoclonal Antibody ior t1.

A subclone ior t1A was obtained from the parental murine ior t1 secreting hybridoma cells which recognize the same epitope on the CD6 molecule.

ior t1A was modified in order to decrease its immunogenicity with a procedure (patent # 0699755 E.P. Bul.) Which simultaneously reduces immunogenicity of the rodent monoclonal antibody while preserving its ligand binding properties in their entirety. Since the antigenicity of an immunoglobulin is dependent on the presence of T-cell antiganic peptides onto their sequence, the immunogenicity of a xenogenic or allogenic antibody could be reduced by replacing the residues included onto the T-cell antigenic sequences which differ from those usually found in another mammalian species antibodies. Of course, the replacement of residues do not include those involved in to the canonical structures or in the Vernier zone. This judicious replacement of residues have no effect on the structural determinants or on the interdomain contacts, thus, ligand binding properties should be unaffected as a consequence of alterations which are limited to the variable region framework residues.

Analysis of Homology of Variable Regions:

The present procedure makes use of the available sequence data for human antibody variable domains compiled by Kabat et al., "Sequences of proteins of Immunological Interest" Fifth edition., Bethesda, Md.; National Inst. of Health, 1994.

In the first step the variable domains of the murine ior t1 heavy or light chain are compared with those corresponding variable domains of the human sequences.

The comparison is made by an automated-computarized method (PC-DOS HIBIO PROSIS 06-00, Hitachi.). The most homologous human variable regions are then compared residue for residue to the corresponding murine regions. This will also define the human subgroup to which each mouse sequence most closely resambles.

Prediction of T-epitopes.

In the second step, the two homologous variable region sequences, mouse and human are analysed for prediction of T-antigenic sequences.

The algorithm AMPHI (Bersofsky et al., (1987) J. Immunol 138: 2213) predicts α Helical sequences. The algorithm SOHHA predicts the strip of helix hydrophobicity (Elliott et al., (1987) J.Immunol. 138: 2949). These algorithms predict T-cell presented fragments of antigenic proteins.

Analysis for immunogenicity reduction.

Those residues in the mouse framework which differ from its human counterpart are replaced by the residues present in the human counterpart. This switching occurrs only with those residues which are at the T-antigenic sequences.

Finally, replacement of those residues responsable for the canonical structures or those involved in the Vernier zone could have a significant effect on the tertiary structure. Hence, they can not be included in the replacement. Additional information about the influence of the proposed replacements on tertiary structure or the binding site, could be obtained from a molecular model of the variable regions.

The method for constructing and expressing the altered antibody.

The following procedures are used to prepare recombinant DNA sequences which incorporate the CDRs of the murine mAb, both light and heavy chains, into human, frameworks that can be used to transfect mammalian cells for the expression of recombinant antibody less immunogenic and with the antigen specificity of the animal monoclonal antibody:

a) Mutagenesis and assembly of variable region domains including CDRs and FRs regions. The PCR-mutagenesis method (Kamman et al., (1989) Nucleic Acids Res.17: 5404) is preferably used to introduce the changes at different positions.

b) Preparation of an expression vector including one variable region and the corresponding human constant region which upon transfection into cells results in the secretion of protein sufficient for affinity and specificity determinations.

c) Co-transfection of heavy and light chain expression vectors in appropriate cell lines.

After about 2 weeks, the cell supernatants are analyzed by ELISA for human IgG production. The samples are then analysed by any method for human IgG capable for binding to specific antigens.

Formulation for Performing In Vitro and In Vivo Diagnostic Studies.

The anti CD6 mAbs can be used for in vitro and in vivo diagnostic purposes in the different clinical forms of Psoriasis, for monitoring patients after topical or systemic treatments, as well as for predicting relapses.

These mAbs purified and dissolved in buffer solution (pH 7.0+/−0.5) containing Sodium Azide (0.01–0.2%) and Bovine Serum Albumin (0.05–0.2%) can be used to quantify the CD6+ T lymphocytes and/or the expression of this molecule on the surface of the lymphoid cells in biological fluids (i.e. blood, cephaloraquidium liquid, synovial liquid) incubating 50 to 200 mL of the sample with 10 to 30 mL of the mAb at concentrations between 0.1 and 3 mg/mL, for 20 to 30 minutes at 4° C. Followed by washing with buffer solution and incubation with immunoglobulins of another animal species conjugated with fluorescent substances (i.e. Fluorescein, Phycoerythrin). The anti CD6 mAbs can be conjugated directly with fluorescent substances by different methods (Coligan, J. E. et al. (Ed.) Current Protocols in immunology, National Institutes of Health. Vol. I:5.3.2. Wiley Interscience) and be used with similar purposes previously described, at concentrations between 5 and 30 mg/mL.

Immunohistochemical Evaluation of the Lesions of Patients with Psoriasis.

The immunohistochemical study of cutaneous lesions or other affected tissues (i.e. articulations) of patients with Psoriasis vulgar can be performed on tissue cryostat sections (i.e. skin) fixed or not in cold acetone, incubating the anti CD6 mAb dissolved between 3 to 10 mg/mL in buffer solution (pH7.0+/−0.5) containing Sodium Azide (0.05–0.2%) and Bovine Serum Albumin (0.05–0.2%) during 30 minutes. Followed by incubation of the tissue sections with biotinylated anti mouse immunoglobulins (i.e. from sheep, DAKO) and Avidin Biotin Peroxidase Complex (i.e. DAKO) during 30 minutes at room temperature. Finally reaction is developed using 3-amino-9-ethyl-carbazole as chromogen (sigma) (Hsu, S. M. at al. (1981) J. Histochem. Cytochem. 29:577). Biopsies must be examined by two specialists and the evaluation of the CD6 is adjusted to a scale of points <10% (+/−), 10–25% (+), 25–50% (++), 50–90% (+++), 90–100% (++++).

Different antibodies to the T lymphocytes CD can be used, anti CD3 (ior t3), anti CD4 (ior t4), anti CD8 (ior t8) and an anti CD45 (ior L3), also an anti Epidermal Growth Factor Receptor mAb (ior egf/r3) as a marker of keratinocytes activation (mozzanica, N. et al. (1994) Acta Derm. Venereol. Suppl. Stockh. 186:171), which allows the evaluation of details of the characteristics of the inflammatory infiltrate of the lesions during the course of the treatment of the disease.

Immunohistochemical Monitoring of the Lesions of the Treated Patients.

Patients treated with anti CD6 monoclonal antibodies can have biopsies of the lesions performed previous to initiating the treatment, during the course of the treatment and after ending the treatment always in the area next to the initial biopsy to evaluate the therapeutical efficacy of the compositions of topical or systemic use. The scale for classifying treatment response can be qualitative in per cent and is established by the index of CD6+ cells over the total CD45+ cells, evaluated in each biopsy.

$$\text{CD6+ cells index} = \frac{\text{Number of CD6+ cells} \times 100}{\text{Number of CD45+ cells}}$$

The index of CD3+ cells, CD4+ cells and CD8+ cells can also be established over the total of CD45+ cells and the index of CD4+ and CD8+ over the total of CD6+ cells.

$$\text{CD3+ cells index} = \frac{\text{Number of CD3+ cells} \times 100}{\text{Number of CD45+ cells}}$$

$$\text{CD4+ cells index} = \frac{\text{Number of CD4+ cells} \times 100}{\text{Number of CD45+ cells}}$$

$$\text{CD8+ cells index} = \frac{\text{Number of CD8+ cells} \times 100}{\text{Number of CD45+ cells}}$$

$$\text{CD4+ cells index} = \frac{\text{Number of CD4+ cells} \times 100}{\text{Number of CD6+ cells}}$$

$$\text{CD8+ cells index} = \frac{\text{Number of CD8+ cells} \times 100}{\text{Number of CD6+ cells}}$$

Immunoscintigraphic Monitoring of Treated Patients.

Another form of evaluating the effect of the treatment with the anti CD6 mAb can be the immunoscintigraphic study in the patient of the expression and distribution of the CD6+ calls during the course of treatment using between 1 and 5 mg of the same mAb conjugated with radioactive isotopes such as 99 m Technetium, using a conjugating method like the one described by Mathers, S. J. at al. (1990) J. Nucl. Med. 31(5):692.

Obtainment of Therapeutic Formulations for Topical and Systemic Use.

The anti CD6 mAbs can be used with therapeutical purposes in different clinical forms of Psoriasis, both with topical and systemic formulations, in single or multiple doses, with one or various treatment cycles according to the severity of the disease.

The topical therapeutic formulations with anti CD6 mAb can be composed by semisolid systems in one or two phases, mainly with hydrophilic formulations that allow the incorporation of the mAb dissolved in sterile buffer solution (pH7.0+/−0.5) in doses between 0.1 mg and 5 mg per each gram of the product. Formulations can be elaborated as gels, jelly, ointment, lotions and creams with a liquid matrix (i.e. water) formulated with gelatin, carboximethylcellulose or similar substances and bases containing glycerine, calcium; additionally the compositions may contain preservatives (i.e. p-hydroxibenzoate) to avoid contamination. The pH must be physiological so as not to affect the characteristics of the mAb. These therapeutic compositions should permit the releasement and penetrability of the mAb in the skin.

Topical treatment should be applied between one and three times a day, over the lesions covered or not and it can be combined with the systemic use (mainly endoveneous) of the same mAb with doses between 0.1 and 1 mg/Kg of patient body weight. It should be diluted in physiological solution for endoveneous use and administered slowly. The endoveneous treatment can be applied independently of the topical administration.

Clinical Follow Up of Treated Patients.

The clinical evolution of the lesions may be used as the main criteria of the evaluation of therapeutic efficacy.

The main variables of response used for measuring the effects of the treatment may be the improvement of the clinical characteristics of the lesions (infiltration, scales, erythema) and the reduction of the area of the lesions.

The degree of severity of the signs of the disease (infiltration, scales and erithema) can be established between the values 0-1-2.

0- no sign.

1- scarce presence.

2- intense presence.

The extension of the treated scales should also be considered, measuring 2 of its diameters and calculating the area of the lesion by multiplying the product of the radios (in centimeters) by p (3.14). The dimension of the scale at time 0 represents 100% and in the subsequent evaluations the per cent of the dimension of the scale is established proportionally.

A PSORIASIS SEVERITY SCORE (PSS) similar to PASI (psoriasis area and severity index) (Fredriksson, T. et al. (1978) Dermatologica 157:238) is obtained with the formula:

$$\frac{\text{infiltration}(0-2) + \text{scales}(0-2) + \text{erithema}(0-2)}{6} \times \% \text{ of the affected area}$$

Responsible to treatment is stratified according to the changes in the PSS when completing the times of evaluations, establishing the following categories (Perkins, W. et al. (1993) Br. J. Dermatol. 129:584)

Clear (>90% improvement in PSS)

Responders (>50% improvement in PUS)

Non-Responders (<50 1 improvement or deterioration in PSS)

Worsening (>50% increase in PSS)

The evaluation times of the response can be assumed up to 12 weeks from the date of initiating the application of the treatment (pretreatment, weeks 1, 2, 3, 4, 6, 8, 12).

EXAMPLE 1

Murine Variable Region of ior t1A Monoclonal Antibodies DNA Sequencing

Cytoplasmic RNA was extracted from about $10^6$ T1 hybridoma cells as described by Faloro et al (Faloro, J. et al. (1989) Methods in Enzimology 65:718).

The cDNA synthesis reaction consisted of 5 ug RNA, 50 mM Tris-HCl, pH 7.5, 75 mM KCl, 10 mM DTT, 3 mM $MgCl_2$, 25 pmol CG2AFOR primer (5'GGAAGCTTAGACCGATGGGGCCTGTTGTTTTG 3') for heavy chain variable region or CK2FOR (5'GGAAGCTTGAAGATGGATACAGTTGGTGCAGC 3') for light chain variable region, 250 uM each of dATF, dTTP, dCTP, dGTP, 15 u ribonuclease inhibitor (RNA guard, Pharmacia) in a total volume of 50 ul.

Samples were heated at 70° C., for 10 min and slowly cooled to 37° C. over a period of 30 min. Then, 100 units MMLV reverse transcriptase (BRL) were added and the incubation at 37° C. continued for 1 hour.

The VH and VK cDNAs were amplified using the PCR as described by Orlandi et al (Orlandi, R. et al. Proc. Natl. Acad. Sci. USA 86.3333–3837, (1989)). For PCR amplification of VH, DNA/primer mixtures consisted of 5 ul cDNA, 25 pmoles CG2A FOR (5'GGAAGCTTAGACCGATGGGGCCTGTTGTTTTG3') and VH1 BACK primers (5'AGGT(G/C)(A/C)A(A/G)CTGCAG(G/C)AGTC(A/T) GG 3').

For PCR amplification of VK, DNA/primers mixtures consisted of 5 ul cDNA, 25 pmoles of CK2 FOR (5'GGAAGCTTGMAGATGGATACAGTTGGTGCAGC 3') and VK10BACK (5'TTGAATTCCAGTGATGTTTTGATGACCCA 3)' primers.

To these mixtures were added 2.5 mM each of dATP, dCTP, dTTP, and dGTP, 5 ul constituents of 10X buffer thermolase and 1 unit of Thermolase(IBI) in a final volume of 50 ul. samples were subjected to 25 thermal cycles at 94° C., 30 sec; 50° C., 30 sec; 72° C., 1 min; and a last incubation for 5 min at 72° C. Amplified VH and VK DNA were purified on Prep. A Gene purification kit (BioRad).

The purified VH and VK DNA were cloned into M13 vector. Clones were sequenced by the dideoxy method using T7 DNA Pol (Pharmacia). See FIGS. 1 and 2.

EXAMPLE 2

Modification of the Variable Domain Sequences of ior t1A Murine Monoclonal Antibody to Humanise the Predicted T-cell Antigenic Sequences The variable region sequences of heavy and light chains of ior t1A were anlyzed for T-cell antigenic sequences. It was made by using the computer algorithm AMPHI, which predict segments of the sequences 11 amino acids in length with an amphipatic helix structure, that is have one side hydrophobic and one side hydrophilic which bind to MHC II molecules.

Onto the variable domain sequence of the heavy chain were predicted 3 segments which are: (It is used Kabat's numbering.).

1. FR 1 between amino acids 2–21,

2. CDR1 and FR2 between amino acids 29–43.

3. CDR3 and FR4 between amino acids 95–111.

The FIG. 1 shows the sequences corresponding to heavy chain.

This murine sequence is compared with the immunoglobulin sequences included in the GeneBank and EMBL database. The most homologous human variable region sequence is determined and also the human subgroup to which the murine sequence most closely resembles is defined. In this case the human sequence founded was an IgM belonging to subgroup III of Kabat.

Both variable region sequences, human and murine are then compared residue for residue and are selected those residues at FR regions which are not involved in the Vernier zone or with the canonical structures. Therefore they could be changed by those residues at the same position onto the human sequence. The positions 13 and 19 are not modified due to the amino acid Lys is present in the same position in other human immunoglobulins belonging to the same subgroup.

For the heavy chain of murine ior t1A were proposed 4 replacements:

1. THR at position 40 by ALA.
2. GLU at position 42 by GLY.
3. THR at position 108 by LEU
4. LEU at position 109 by VAL.

The game procedure applied to the light chain (FIG. 2) rendered a set of overlaping segments from aminoacid 2 aminoacid 69.

After the analysis we proposed 7 replacements in FRs 1 and 2 at positions: 3, 11, 12, 15, 17, 41 and 43.

1. LYS at position 3 by GLN
2. MET at position 11 by LEU
3. TYR at position 12 by SER
4. LEU at position 15 by VAL
5. GLU at position 17 by ASP
6. TRP at position 41 by GLY
7. SER at position 43 by ALA

EXAMPLE 3

Construction of Mutant Heavy and Light Chain Variable Region of ior t1A by PCR Mutagenesis The changes in the amino acids of mutant heavy and light chain variable region were constructed using PCR mutagenesis (Kammann, M. et al. (1989) Proc. Natl. Acad. Sci. USA, 86: 4220).

Briefly: Two amplification by PCR: the reaction mixture was: 0.5 ul the VH supernatant of single strand DNA cloned in M13, 25 pmoles mutagenic oligo 1 or 2, 25 pmoles mutagenic oligo 3 or 4 primers (See below the primers sequences). To these mixtures were added 2.5 mM each of dATF, Dttp, dCTP, and dGTP, 5 $\mu$l constituents of 10X Vent Polymerase buffer (NSB) and 1 unit of Vent DNA Polymerase (NEB) in a final volume of 50 ul. Samples were subjected to 12–15 thermal cycles at 94° C., 30 sec; 50° C., 30 sec; 75° C., 1 min; and a last incubation for 5 min at 75° C. The products of both PCRs are joined in a second PCR using the outside primers only (3 and 4). Amplified VH DNA were purified on Prep. A Gene purification kit (BioRad).

For the changes in the heavy chain, FR1 in the positions 5, 7, 11, 12 and 13 the primers used, were:

Primer 1:
5'TGG GTT CGC CAG GCT CCG GGG AAG AGG CTG GAG 3'.
Primec 3;
5'GTA AMA CGA CGG CCA GT 3'.
These primers are combined in one PCR.
Primer 2:
5'CTC CAG CCT CTT CCC CGG AGC CTG GCG AAC CCA 3'.
Primer 4:
5'AGC GGA TAA CAA TTT CAC ACA GGA 3'.
These primers are combine in one PCR. Then, the products of both PCRs are combined in one PCR using 3 and 4 primers.

For the changes in the POSITION 108 and 109, the primers designed were:

Primer 1:
5'GGC CAA GGC ACC CTT GTC ACC GTC TCC 3'.
Primer 3:
5'GTA AAA CGA CGG CCA GT 3'.
These primers are combined in one PCR.
Primer 2:
5'GGA GAC GGT GAC AAG GGT GCC TTOG GCC 3'.
Primer 4:
5'AGC GGA TAA CAA TTT CAC ACA GGA 3'.
These primers are combined in one PCR. Then, the products of both PCRs are combined in one PCR using 3 and 4 primers.

In the light chain for the changes in the FR1 in the residues 3, 11, 12, 15 and 17, the primers were designed as:
PRIMER 1;
5'TGT GAC ATC CAG ATG ACC CAG TCT CCA TCC TCC CTG TCT GCA TCG CAT CGG TGG GAG ACA GAG TCA CC 3'
PRIMER 3: 5'GTA AAA CGA CGG CCA GT 3'
These primers are combined in one PCR
PRIMER 2:
5'GGT GAC TCT GTC TCC CAC CGA TGC AGA CAG GGA GGA TGG AGA CTG GGT CAT CTG GAT GTC ACA 3'
PRIMER 4: 5'ACT GGC CGT CGT TTT TAC 3'
These primers are combined in one PCR.
The products of both PCRs are combined in one PCR using primers 3 and 4.

For the changes in the residues 41 and 43 in the FP2 the primers were:
PRIMER 1: 5'CAG AAA CCA GGG AAA GCT CCT AAG ACC CTG 3'
PRIMER 3: 5'GTA AAA CGA CGG CCA T 3'
These primers are combined in one PCR.
PRIMER 2: 5'CAG GGT CTT AGG AGC TTT CCC TGG TTT CTG 3'
PRIMER 4: 5'ACT GGC CGT CGT TTT TAC 3'
These primers are combined in one PCR.
The products of both PCRs are combined in one using primers 3 and 4.

EXAMPLE 4

Pharmaceutical Formulation for Topic Use in Cutaneous Lesions of Patients with Psoriasis Vulgar The ior t1 mAb was purified and dissolved (50.00 mg) in sterile buffer solution (10 mL pH7.0+/−0.5) containing Monobasic Sodium Phosphate 4.50 mg , Dibasic Sodium Phosphate 18.00 mg , Sodium Chloride 86.00 mg, Polysorbate 80 1.952 $\mu$L, Water for injection. The solution containing the mAb was added to a jelly base.

The therapeutic jelly was elaborated with a buffer solution having a composition similar to the one described for the mAb (pH 7.0+/−0.5).

EXAMPLE 5

Histological Study of Cutaneous Lesions of Patients with Psoriasis Vulgar

The immunohistochemical study of the cutaneous lesions of patients with Psoriasis vulgar was performed on cryostat sections of skin tissue, using the mAb ior t1 in parallel with different mAbs directed against CD of T lymphocytes. mAbs ior t3 (anti CD3), ior t4 (anti CD4), ior t8 (anti CD8), ior L3 (anti CD45) and DAKO CD6 (anti CD6), as control, as well as ior egf/r3 (anti Epidermal Growth Factor Receptor) were used. Followed by incubation of tissue sections with biotinylated anti mouse immunoglobulins (i.e. from sheep, DAKO) and Avidin Biotin Peroxidase Complex (i.e. DAKO). Finally reaction is developed using 3-amino-9-ethyl-carbazole as chromogen (Sigma). Biopsies were examined by two specialists and the evaluation of the CD6 was adjusted to a scale of points <10% (+/−), 10–25% (+), 25–50% (++), 50–90% (+++), 90–100% (++++).

Patients treated with anti CD6 monoclonal antibodies had biopsies of the lesions performed previous to initiating the treatment and at the end of the third week of treatment in the area next to the initial biopsy . The scale for classifying treatment response was qualitative in per cent and established by the index of CD6+ cells over the total CD45+ cells , evaluated in each biopsy. The per cent of the expression of the anti Epidermal Growth Factor receptor (EGF-R) in the different stratus of the skin was determined as well as the modifications of the histological characteristics typical of the disease.

In the inflammatory infiltrate characteristic of Psoriasis Vulgar was found to exists an important Expression (+++) of the CD6+ T lymphoid phenotype.

The CD3+ lymphocytes represent approximately 100% of the CD45+ cells.

The CD6+ cells represents approximately between 60% and over 90% of the CD3+ cells.

The CD6+ cells (ior t1) represents approximately between 30% and 50% of the CD6+ cells (DAKO CD6).

The expression of the EGF-R in keratinocytes was elevated showing a reticulated pattern.

The predominance of the expression of the CD6 molecule in the T lymphocytes of the inflammatory infiltrate results significant since it is a molecule characteristic of activated T lymphocytes. This makes us believe that this might constitute a leukocitary adhesion molecule of the T lymphocytes, initially activated in the skin by the penetration of exogenous antigens or modified self antigens. Necessary this for the interaction with specific cellular determinants of the skin activated during the response to the said antigens.

EXAMPLE 6

Clinical Response of Patients with Psoriasis Vulgar to the Topical Therapy with ior t1 mAb A clinical trial of patients with a diagnosis of Psoriasis Vulgar in relapse with lesions characteristic of this disease was performed. The study was scheduled in two groups of fourteen patients per group difined according to the jelly received for topical treatment (ior t1 mAb or vehicle). The topical therapeutic formulation was conformed by a jelly base or vehicle (Sodium Carboximethylcelulose v/v Propilenglycol, Methylparabeno, Trietanolamine) in which the mAb was incorporated. Treatment was applied two times a day during 21 days without occlusion of the lesions treated.

Psoriatic plaque lesions whiten in all the patients treated with ior t1 mAb (FIG. 4). This result corresponds with post treatment biopsy performed 21 days after initiating application of the mAb. A decrease of T lymphocyte infiltrate and of the expression of the EGF-R in keratinocytes as well as a regression in the histological signs characteristic of the disease were observed.

EXAMPLE 7

Clinical Response of Psoriasis Vulgaris Patients After Scaling-down Topical Treatment with ior t1 Monoclonal Antibody A Pilot Clinical Trial in 19 confirmed long-lasting psoriasis vulgaris patients with more than 10% and less than 25% of their skin affected was performed. Three different groups of 6, 7 and 6 patients received a therapeutic topical formulation containing 0.3, 1 and 3 mg of ior t1A mAb/gram of jelly respectively, in a vehicle jelly consisting of Sodium Carboximethylcelulose A/V, Propylenglicol, Methylparabene, Propylparabene and Triethanolamine. Patients were topicaly treated 2 times a day during 21 days.

PASI (Psoriatic Area and Severity Index) was scored and analised and human anti mouse antibody (HAMA) response in the sera of patients was also studied. The best results related to clinical response (PASI) and disease free interval were obtained in the group treated with the lower amount of ior t1 mAb (0.3 mg), as well as the HAMA (Human Anti-Mouse Antibody) titres and the amount of patients by group developing it were also higher in that group. Moreover, the presence of anti-idiotype antibodies in patient's sera studied by means of blocking ELISA (Enzyme Linked Immunosorbent Assay) and FACS (Fluorescent Activating Cell Sorter) were more frequent and much higher in those patients treated with the lower doses of 0.3 mg per gram of jelly.

EXAMPLE 8

Clinical Response of one Patient with the Severe Form of Generalized Psoriasis to the Endoveneous Treatment with the ior t1 mAb.

Female patient, 56 years old with a history of Psoriasis with psoriatic arthropathy diagnosed approximately 17 years ago. In the last 5 years the patient has suffered frequent and intense crisis, causing frequent hospitalizations. Crisis started with erithematosquamous generalized lesions, pain in articulations and muscles, feverish, generalized edemas and malaise. This general status persists and 21 days later new lesions appear in the axilary region, the neck and around the breasts, with ulcerations and infected serose secretion accompanied by fever. Due to the torpid evolution of the disease and the intolerance to all previous treatments including steroid creams, treatment with methotrexate is indicated administering 3 cycles with a total doses of 15 mg. No clinical response was observed.

Single endoveneous dose of ior t1 mAb at 0.6 mg/Kg of body weight, administered slowly, diluted in 200 mL of Saline Solution 0.9.

Simultaneously a therapeutical jelly containing ior t1 mAb at a concentration of 3 mg of mAb/ g of jelly was applied 2 Times a day in all the lesions during two days.

The patient starts to improve her general status and dermatological picture around the 6th day of treatment. At day 21 an evaluation was performed and 60% of the body surface was without lesions and the rest of the skin showed improvement of the clinical signs of the disease. The patient referred improvement of the symptoms in articulations, having a good general status, normal vital signs and routine laboratory tests.

After 30 days the patient maintains complete regression of the symptoms of the disease.

A viable culture of T1 hybridoma cells, as described in the above-identified application, namely IOR-T1A, was deposited in accordance with the Budapest Treaty with the European Collection of Cell Cultures, Centre for Applied Microbiology and Research, Salisbury, Wiltshire, SP4 OJG, United Kingdom, on Nov. 26, 1996. The accession number is for this deposit is 96112640. All restrictions and conditions by the depositors/applicants upon availability of the cell culture to the public will be irrevocably removed upon granting of a patent based on the above-identified application.

BRIEF DESCRIPTION OF THE FIGURES

FIGS. 1 and 2

Figure 4:
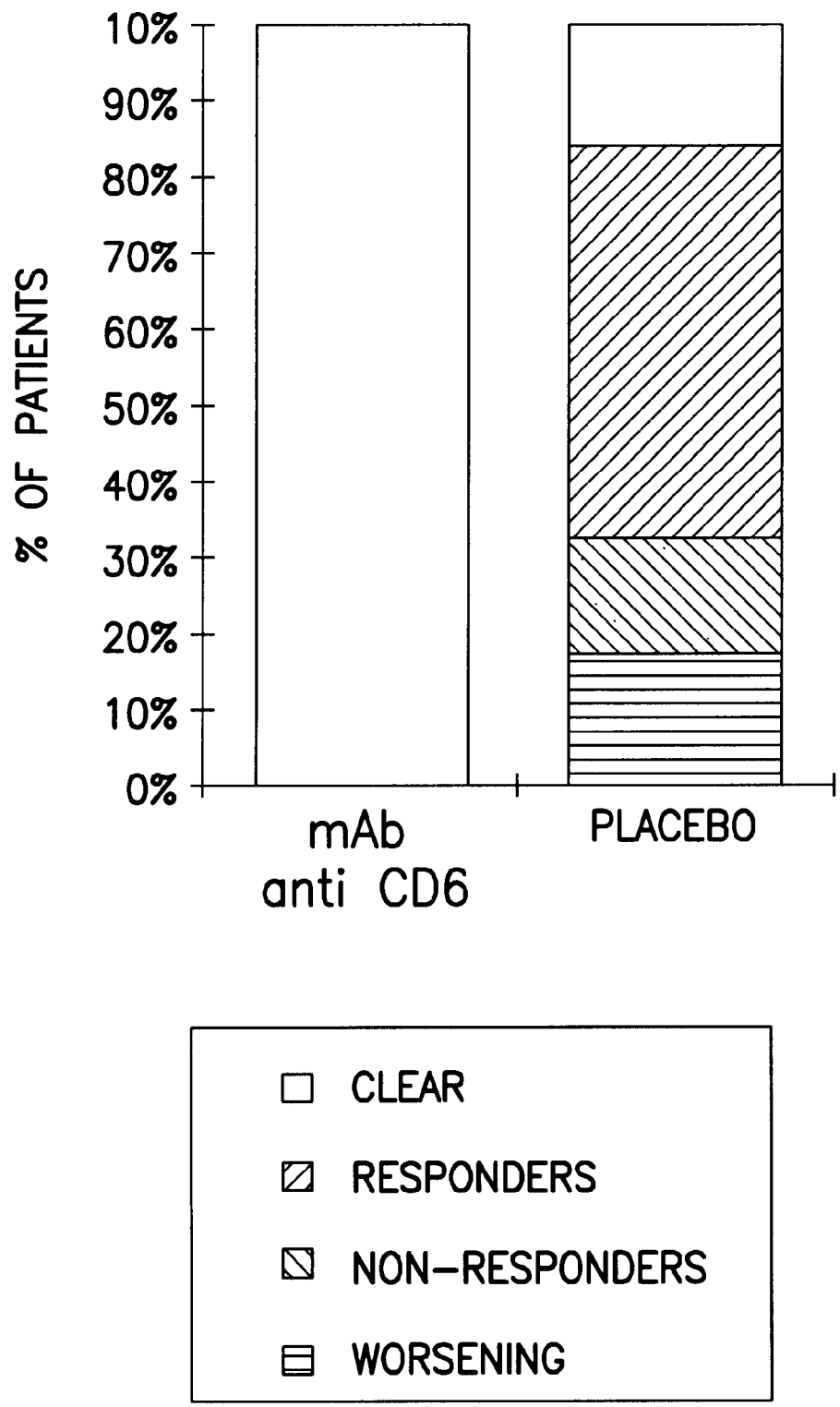
Figure 5:
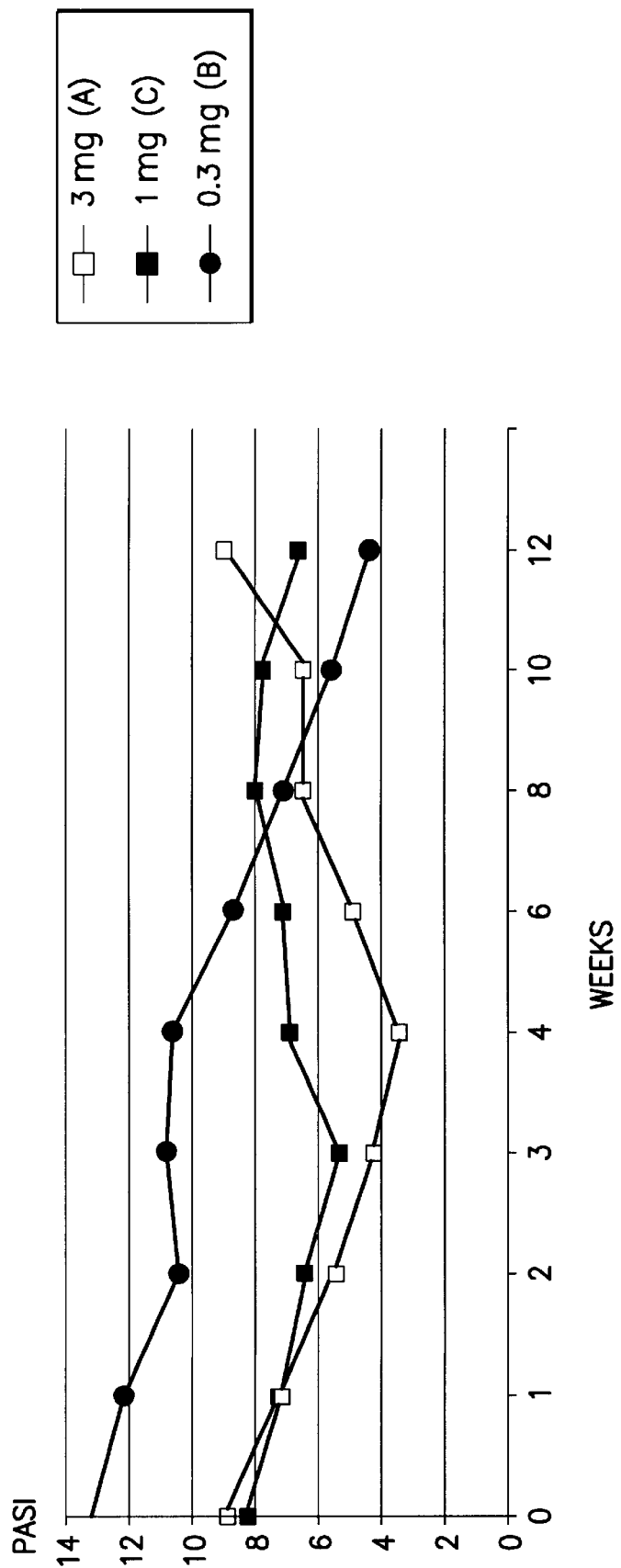

Analysis for the modification by way of humanization of the variable regions of heavy and light chains of monoclonal antibody ior t1A:

FIG. 1: Sequence of the variable region of heavy chain of the murine ior t1A monoclonal antibody.

FIG. 2: Sequence of the variable region of light chain of the murine ior t1A monoclonal antibody.

A: Sequence of the variable region of heavy chain or light chain of ior t1A murine mAb.

B: Sequence of the variable region of the most homologous human immunoglobulin.

C: Sequence of the modified variable region of ior t1A.

shading: predicted T-cell antigenic sequences.

Underlined amino acids residues: amino acids involved in tertiary structure.

Bold font: complementarity determining regions.

Amino acids residues in boxes: replacements which are proposed.

The description is idem for both, heavy and light chains.

FIG. 3

The results of the expression of the CD6 antigens in lymphocytes of the inflammatory infiltrates characteristic of the cutaneous lesions of patients with Psoriasis Vulgar are shown. This evaluation was performed in cryostat sections biopsies of skin affected by plaques lesions localized in the upper and/or lower limbs and/or thorax-abdomen. The histological evaluation was performed previous to the immunohistochemistry study.

FIG. 4

The evaluation of the therapeutic efficacy of the anti CD6 mAbs used in the treatment of the Psoriasis was performed considering the following variables: infiltration, scales, erythema and the size of the area of the lesion. The great of severity was established between the values zero-1–2. The extension of the treated plaques was established measuring to of its diameters. A Psoriasis Severity Score (PSS) similar to the PASI (Psoriasis Area and Severity Index) was obtained and the response to treatment was stratified according to the changed in the PSS at the end of the designated evaluation time. The following categorizes was established: Clear, Responders, Non-Responders and Worsening.

FIG. 5

Clinical response of patients treated with a topical formulation containing 0.3, 1 or 3 mg of ior t1A mAb/gram of jelly respectively was evaluated by PASI (Psoriatic Area and Severity Index) and the human anti mouse antibody (HAMA) response in the sera of these patients was also studied. The best results related to clinical response (PASI) and disease free interval were obtained in the group treated with the lower amount of ior t1 mAb (0.3 mg), as well as the HAMA titres and the amount of patients by group developing it were also higher in that group. Moreover, the presence of anti-idiotype antibodies in patient's sera were more frequent and much higher in those patients treated with the lower doses of 0.3 mg per gram of jelly.

FIG. 6

Endovenous treatment was applied with the ior t1 mAb to a 56 years old patient with a history of Psoriasis with psoriatic arthropathy diagnosed approximately 17 years ago. Presenting now a severe form of generalized psoriasis characterized by erithematosquamous generalized lesions, pain in articulations and muscles, feverish, generalized edemas and malaise. This general status did not respond to treatment including methotrexate. Treatment was performed with single endoveneous dose of ior t1 mAb at 0.6 mg/Kg of body weight, administered slowly, diluted in 200 mL of Saline Solution 0.9%. Simultaneously a therapeutical jelly containing ior t1 mAb at a concentration of 3 mg of mAb/g of jelly was applied 2 times a day in all the lesions during two days, for a total of 224 g. of therapeutic jelly. The clinical response and the immunohistochemistry laboratory results were evaluated weekly. Photographs of the evolution of the cutaneous lesions are shown (the day before and 21 days after the treatment).

In accordance with the invention, there are provided monoclonal antibodies recognizing human CD6 in accordance with claims 1 or 2, wherein the subclon ior t1A obtained from the hybridoma of the same name (Deposit Number: pending) has a variable region of its heavy chain of sequence:

```
GLU VAL GLN LEU VAL GLU SER GLY GLY GLY LEU VAL
LYS PRO GLY GLY SER LEU LYS LEU SER CYS ALA ALA
SER GLY PHE LYS PHE SER ARG TYR ALA MET SER TRP
VAL ARG GLN THR PRO GLU LYS ARG LEU GLU TRP VAL
ALA THR ILE SER SER GLY GLY SER TYR ILE TYR TYR
PRO ASP SER VAL LYS GLY ARG PHE THR ILE SER ARG
ASP THR SER SER ASN THR ALA TYR MET GLN LEU SER
SER LEU ARG SER GLU ASP THR ALA MET TYR TYR CYS
ALA ARG ARG ASP TYR ASP LEU ASP TYR PHE ASP SER
TRP GLY GLN GLY THR THR LEU THR VAL SER SER and the variable region of
its light chain of sequence:

ASP ILE LYS MET THR GLN SER PRO SER SER MET TYR
ALA SER LEU GLY GLU ARG VAL THR ILE THR CYS LYS
ALA SER ARG ASP ILE ARG SER TYR LEU THR TRP TYR
GLN GLN LYS PRO TRP LYS SER PRO LYS THR LEU ILE
TYR TYR ALA THR SER LEU ALA ASP GLY VAL PRO SER
ARG PHE SER GLY SER GLY SER GLY GLN ASP TYR SER
LEU THR ILE SER SER LEU GLU SER ASP ASP THR ALA
THR TYR TYR CYS LEU GLN HIS GLY GLU SER PRO PHE
THR PHE GLY SER GLY THR LYS LEU GLU ILE LYS ARG
ALA
```

In accordance with the invention, there are also provided monoclonal antibodies recognizing human CD6 in accordance with claims 1 to 3, which is a humanized variant of subclon ior t1A, and a variable region of its heavy chain has the sequence:

GLU VAL GLN LEU VAL GLU SER GLY GLY GLY LEU VAL

LYS PRO GLY GLY SER LEU LYS LEU SER CYS ALA ALA

SER GLY PHE LYS PHE SER ARG TYR ALA MET SER TRP

VAL ARG GLN ALA PRO GLY LYS ARG LEU GLU TRP VAL

ALA THR ILE SER SER GLY GLY SER TYR ILE TYR TYR

PRO ASP SER VAL LYS GLY ARG PHE THR ILE SER ARG

ASP ASN VAL LYS ASN THR LEU TYR LEU GLN MET SER

SER LEU ARG SER GLU ASP THR ALA MET TYR TYR CYS

ALA ARG ARG ASP TYR ASP LEU ASP TYR PHE ASP SER

TRP GLY GLN GLY THR LEU VAL THR VAL SER SER and the variable region of
its light chain has the sequence:

ASP ILE GLN MET THR GLN SER PRO SER SER LEU SER

ALA SER VAL GLY ASP ARG VAL THR ILE THR CYS LYS

ALA SER ARG ASP ILE ARG SER TYR LEU THR TRP TYR

GLN GLN LYS PRO GLY LYS ALA PRO LYS THR LEU ILE

TYR TYR ALA THR SER LEU ALA ASP GLY VAL PRO SER

ARG PHE SER GLY SER GLY SER GLY GLN ASP TYR SER

LEU THR ILE SER SER LEU GLU SER ASP ASP THR ALA

THR TYR TYR CYS LEU GLN HIS GLY GLU SER PRO PHE

THR PHE GLY SER GLY THR LYS LEU GLU ILE LYS ARG

ALA

In addition, the Information for SEQ ID: 1 and the Sequence Description for SEQ ID NO:1, as well as the same Information and Sequence Description for ID Nos. 2–4 are all incorporated herein by reference and is exactly as set forth in the computer readable form (CRF) disc of the "Sequence Listing" or in the substitute paper copy of the "Sequence Listing".

"As referenced hereinabove in the descriptions of FIGS. 1–2 of the instant patent application, the sequences in lines or rows B correspond to human sequences of the variable regions with a high homology with the murine anti-CD6 antibody. These sequences are conventional and well-known in the art, and in the present patent application they were only used therein so as to be compared with the sequences of the murine antibody in the procedure to humanize the murine anti-CD6. Thus, these human sequence are not claimed nor do they form any part of the present invention as defined and claimed in the case.

In the present application, applicants claim, as their invention, the sequences for heavy and light chains of the murine antibody (sequences 1 and 2), and the humanized version of said antibody (sequences 3 and 4). More particularly, these sequences are:

Sequence 1: represents the murine variable region of the heavy chain (anti-CD6 antibody);

Sequence 2: represents the murine variable region of the light chain (anti-CD6 antibody);

Sequence 3: represents the humanized variable region of the heavy chain (anti-CD6 antibody); and Sequence 4: represents the humanized variable region of the light chain (anti-CD6 antibody).

All four sequences of the present invention are unique sequences which are all novel and which are believed to be patentable."

---

What is claimed is:

1. A monoclonal antibody that is a humanized sub clone of IOR-T1A produced by the hybridoma deposited with ECACC, CAMR under accession number 96112640, having heavy and light chains with humanized variable regions.

2. A monoclonal antibody according to claim 1, comprising:

a heavy chain having a variable region with the following sequence:

Glu Val Gln Leu Val Glu Ser Gly Gly Gly Leu Val Lys Pro Gly Gly Ser Leu Lys Leu Ser Cys Ala Ala Ser Gly Phe Lys Phe Ser Arg Tyr Ala Met Ser Trp Val Arg Gln Thr Pro Glu Lys Arg Leu Glu Trp Val Ala Thr Ile Ser Ser Gly Gly Ser Tyr Ile Tyr Tyr Pro Asp Ser Val Lys Gly Arg Phe Thr Ile Ser Arg Asp Asn Val Lys Asn Thr Leu Tyr Leu Gln Met Ser Ser Leu Arg Ser Glu Asp Thr Ala Met Tyr Tyr Cys Ala Arg Arg Asp Tyr Asp Leu Asp Tyr Phe Asp Ser Trp Gly Gln Gly Thr Thr Leu Thr Val Ser Ser
(SEQ. ID. NO. 1)

and a light chain having a variable region with the following sequence:

Asp Ile Lys Met Thr Gln Ser Pro Ser Ser Met Tyr Ala Ser Leu Gly Glu Arg Val Thr Ile Thr Cys Lys Ala Ser Arg Asp Ile Arg Ser Tyr Leu Thr Trp Tyr Gln Gln Lys Pro Trp Lys Ser Pro Lys Thr Leu Ile Tyr Tyr Ala Thr Ser Leu Ala Asp Gly Val Pro Ser Arg Phe Ser Gly Ser Gly Ser Gly Gln Asp Tyr Ser Leu Thr Ile Ser Ser Leu Glu Ser Asp Asp Thr Ala Thr Tyr Tyr Cys Leu Gln His Gly Glu Ser Pro Phe Thr Phe Gly Ser Gly Thr Lys Leu Glu Ile Lys Arg Ala
(SEQ. ID. NO. 2).

3. A humanized variant of sub-clone IOR T1A of IgG1 isotype of the monoclonal antibody according to claim 1, comprising:

a heavy chain having a variable region with the following sequence:

Glu Val Gln Leu Val Glu Ser Gly Gly Gly Leu Val Lys Pro Gly Gly Ser Leu Lys Leu Ser Cys Ala Ala Ser Gly Phe Lys Phe Ser Arg Tyr Ala Met Ser Trp Val Arg Gln Ala Pro Gly Lys Arg Leu Glu Trp Val Ala Thr Ile Ser Ser Gly Gly Ser Tyr Ile Tyr Tyr Pro Asp Ser Val Lys Gly Arg Phe Thr Ile Ser Arg Asp Asn Val Lys Asn Thr Leu Tyr Leu Gln Met Ser Ser Leu Arg Ser Glu Asp Thr Ala Met Tyr Tyr Cys Ala Arg Arg Asp Tyr Asp Leu Asp Tyr Phe Asp Ser Trp Gly Gln Gly Thr Leu Val Thr Val Ser Ser
(SEQ. ID. NO. 3)

and a light chain having a variable region with the following sequence:

Asp Ile Gln Met Thr Gln Ser Pro Ser Ser Leu Ser Ala Ser Val Gly Asp Arg Val Thr Ile Thr Cys Lys Ala Ser Arg Asp Ile Arg Ser Tyr Leu Thr Trp Tyr Gln Gln Lys Pro Gly Lys Ala Pro Lys Thr Leu Ile Tyr Tyr Ala Thr Ser Leu Ala Asp Gly Val Pro Ser Arg Phe Ser Gly Ser Gly Ser Gly Gln Asp Tyr Ser Leu Thr Ile Ser Ser Leu

Glu Ser Asp Asp Thr Ala Thr Tyr Tyr Cys Leu Gln
His Gly Glu Ser Pro Phe Thr Phe Gly Ser Gly Thr
Lys Leu Glu lle Lys Arg Ala
(SEQ. ID. NO. 4).

4. Monoclonal antibodies according to claim 1, which are IgG2a isotype.

5. Humanized monoclonal antibodies according to claim 1 which are IgG1 isotype.

6. Pharmaceutical composition for the treatment of Psoriasis which contains the monoclonal antibodies according to any one of claims 2 to 3.

7. Monoclonal antibodies according to claim 2, which are IgG2a isotype.

* * * * *